(12) United States Patent
Rowan

(10) Patent No.: US 6,673,883 B1
(45) Date of Patent: Jan. 6, 2004

(54) POLYMERS CONTAINING ZWITTERIONIC MONOMERS

(75) Inventor: Lee Rowan, Warwickshire (GB)

(73) Assignee: Biocompatibles UK Limited, Surrey (GB)

( * ) Notice: Subject to any disclaimer, the term of this patent is extended or adjusted under 35 U.S.C. 154(b) by 0 days.

(21) Appl. No.: 09/341,476

(22) PCT Filed: Jan. 12, 1998

(86) PCT No.: PCT/GB98/00070
§ 371 (c)(1),
(2), (4) Date: Jul. 12, 1999

(87) PCT Pub. No.: WO98/30615
PCT Pub. Date: Jul. 16, 1998

(30) Foreign Application Priority Data

Jan. 10, 1997 (GB) ............................................. 9700390
Sep. 5, 1997 (GB) ............................................. 9718909

(51) Int. Cl.⁷ .......................... C08F 12/18; C08F 20/10; C08F 20/22
(52) U.S. Cl. ...................... 526/277; 526/278; 526/310; 526/312; 526/328; 526/328.5; 427/372.2; 427/383.1; 427/387; 427/388.5
(58) Field of Search ............... 526/277, 278, 526/310, 312, 328, 328.5, 279; 427/372.2, 383.1, 387, 388.5

(56) References Cited

U.S. PATENT DOCUMENTS

| | | | |
|---|---|---|---|
| 3,453,136 A | 7/1969 | Bylsma et al. | 117/72 |
| 4,213,886 A | 7/1980 | Turner | 260/29.6 MM |
| 4,945,145 A * | 7/1990 | Bruylants et al. | 526/279 |
| 5,162,420 A | 11/1992 | Chang et al. | 524/457 |
| 5,302,669 A * | 4/1994 | Furukawa et al. | 525/440 |
| 5,648,442 A * | 7/1997 | Bowers et al. | 526/277 |
| 6,083,257 A * | 4/2000 | Taylor et al. | 623/1 |
| 6,183,506 B1 * | 2/2001 | Penn et al. | 623/1.15 |

FOREIGN PATENT DOCUMENTS

| | | | |
|---|---|---|---|
| EP | 0075957 A2 | 4/1983 | C08F/220/28 |
| EP | 0412385 A1 | 2/1991 | C08F/230/08 |
| FR | 1549939 | 12/1968 | |
| JP | 7-51355 | 2/1995 | A61L/31/00 |
| WO | 93/01221 | 1/1993 | C08F/246/00 |
| WO | WO 97/16133 | 5/1997 | |

OTHER PUBLICATIONS

Polymer, vol. 38, No. 20,1997, pp. 5173–5178, "Silicon Secondary Crosslinked IPN Based on Poly(Methyl Acrylate–Co–Hydroxylethyl Acrylate) and SiO₂", Yin et al.

Cardiovascular Division, Biocompatibles Ltd., "Novel Phosphorylcholine Based Hydrogel Poluymers: Developments in Medical Device Coatings", Stratford et al.

Database WPI, Section Ch., Week 9403, Derwent Publications Ltd., London, GB, AN 94–022958, XP002060534 (abstract).

Database WPI, Section Ch., Week 9346, Derwent Publications Ltd., London, GB, An 93–365463, XP002060535 (abstract).

Database WPI, Section Ch., Week 9312, Derwent Publications Ltd., London, GB, AN 93–096841, XP002060536 (abstract).

* cited by examiner

Primary Examiner—David W. Wu
Assistant Examiner—Tanya Zalukaeva
(74) Attorney, Agent, or Firm—Sughrue Mion, PLLC

(57) ABSTRACT

A cross-linkable polymer formed from monomer including a) a hydroxyl-group containing monomer of the formula I $$H_2C = \overset{R^{26}}{\underset{|}{C}} - \overset{O}{\underset{||}{C}} - A^1 - B^9 - R^{13} - (OH)_n$$

in which $R^{26}$ is hydrogen or a $C_{1-4}$-alkyl group;
$A^1$ is —O— or —$NR^{27}$— where $R^{27}$ is hydrogen or a $C_{1-4}$-alkyl group or a group $B^9R$—$(OH)_n$;
$B^9$ is a bond, a straight or branched alkylene, oxa alkylene or oligooxa alkylene group;
$R^{13}$ is a n+1 functional $C_{1-24}$ alkylene group which may be substituted, and
n is an integer of one or more;

b) a reactive monomer of the formula (II)

$$H_2C = \overset{R^{19}}{\underset{|}{C}} - \overset{O}{\underset{||}{C}} - A^2 - R^{12} - A^3 - Si(OR^{16})_3$$

in which $R^{19}$ is hydrogen or a $C_{1-4}$-alkyl group;
$A^2$ is —O— or —$NR^{21}$— where $R^{21}$ is hydrogen, or a $C_{1-4}$-alkyl group
$R^{12}$ is a $C_{1-24}$ straight or branched alkylene, oxaalkylene or oligo oxaalkylene group in which each alkylene group has 1 to 6 carbon atoms;
$A^3$ is a bond or —O—; and
each $R^{16}$ is independently selected from $C_{1-6}$-alkyl groups. Preferably the polymer includes a zwitterionic monomer and is useful for providing stable biocompatible coatings on substrates.

29 Claims, No Drawings

POLYMERS CONTAINING ZWITTERIONIC MONOMERS

This invention relates to new polymeric materials especially suitable for use in biomedical applications, and processes for their production and use.

According to the present invention there is provided a crosslinkable polymer formed from monomers including a) a hydroxyl-group containing monomer of the general formula I

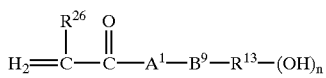

in which $R^{26}$ is hydrogen or $C_{1-4}$-alkyl group $A^1$ is —O— or —$NR^{27}$— where $R^{27}$ is hydrogen or a $C_{1-4}$-alkyl group or a group $B^9R$—$(OH)_n$;

$B^9$ is a bond, a straight or branched alkylene, a oxa alkylene or oligooxa alkylene group;

$R^{13}$ is a n+1 functional (optionally substituted) $C_{1-24}$ alkylene group, n is an integer of one or more; and b) a reactive monomer of the general formula (II)

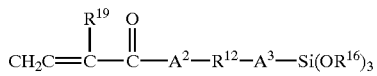

in which $R^{19}$ is hydrogen or a $C_{1-4}$-alkyl group or $A^2$ is —O— or —$NR^{21}$— where $R^{21}$ is hydrogen, or a $C_{1-4}$-alkyl group $R^{12}$ is $C_{1-24}$ straight or branched alkylene, oxaalkylene or oligo oxaalkylene group in which each alkylene group has 1 to 6 carbon atoms $A^3$ is a band or —O— each $R^{16}$ independently selected from $C_{1-6}$-alkyl groups.

In hydroxyl group containing monomer of the general formula I, $R^{26}$ is preferably hydrogen or methyl, most preferably methyl. $A^1$ is preferably —O—. $B^9$ is preferably a bond.

$R^{13}$ is preferably selected from $C_{2-6}$-alkylene groups, most preferably $C_{2-4}$-alkylene, most preferably propylene. The monomer I may consist of a mixture of compounds having different groups $R^{13}$. Preferably, in such a mixture, all groups $R^{13}$ have the same number of carbon atoms, but may comprise a mixture of different isomers. For instance where the group $R^{13}$ is propylene, it may consist of a mixture of 1,2-propylene and 1,3-propylene.

In the reactive monomer of the general formula II, $R^{19}$ is preferably selected from hydrogen and methyl groups, most preferably $R^{19}$ is methyl. $A^2$ is preferably —O—. $A^3$ is preferably —O—. $R^{12}$ is preferably $C_{2-6}$-alkylene, preferably $C_{2-4}$-alkylene. Again, the monomer of the formula II may comprise a mixture of compounds having different groups $R^{12}$.

$R^{16}$ is selected from $C_{1-6}$-alkyl groups, preferably $C_{1-2}$-alkyl groups.

Preferred polymers are made from monomers including a zwitterionic monomer of the general formula III

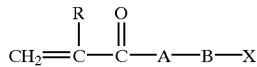

wherein B is a straight or branched alkylene, oxaalkylene or oligo-oxaalkylene chain optionally containing one or more fluorine atoms up to and including perfluorinated chains or, if X contains a carbon—carbon chain between B and the zwitterionic moiety or if Y contains a terminal carbon atom bonded to B, a valence bond;

X is a zwitterionic group

R is hydrogen or a $C_1$–$C_4$ alkyl group; and

A is —O— or —$NR^1$— where $R^1$ is hydrogen or a $C_1$–$C_4$ alkyl group or $R^1$ is —B—X where B and X are as defined above.

In compounds of formula (III) it is preferred that K and B contain up to 12 carbon atoms in total.

In the zwitterionic monomer of the general formula III, R is preferably selected from hydrogen and methyl, and is most preferably methyl.

Preferably $B^9$ is an alkylene group of formula —$(CR^3_2)_a$—, wherein the groups —$(CR^3_2)$— are the same or different, and in each group —$(CR^3_2)$— the groups $R^3$ are the same or different and each group $R^3$ is hydrogen, fluorine or $C_{1-4}$ alkyl or fluoroalkyl, preferably hydrogen, and a is from 1 to 12, preferably 1 to 6;

an oxaalkylene group such as alkoxyalkyl having 1 to 6 carbon atoms in each alkyl moiety, more preferably —$CH_2O(CH_2)_4$—; or an oligo-oxaalkylene group of formula —$[(CR^4_2)_bO]_c$$(CR^4_2)_b$— where the groups —$(CR^4_2)$— are the same or different and in each group —$(CR^4_2)$— the groups $R^4$ are the same or different and each group $R^4$ is hydrogen, fluorine or $C_{1-4}$ alkyl or fluoroalkyl, preferably hydrogen, and b is from 1 to 6, preferably 2 or 3 and c is from 2 to 11, preferably 2 to 5; or if X contains a carbon—carbon chain between B and the centre of permanent positive charge or if Y contains a terminal carbon atom, a valence bond.

Preferred groups B include alkylene, oxaalkylene and oligo-oxaalkylene groups of up to 12 carbon atoms optionally containing one or more fluorine atoms.

Preferred zwitterionic groups on zwitterionic monomer III are groups in which the cationic moiety is based on a quaternary ammonium group and the anionic moiety is based on a phosphate group. Preferred zwitterionic groups are ammonium phosphate ester zwitterionic groups. Preferably the ammonium is quaternary ammonium and the phosphate group is a diester group, or amide analogue. Usually the cationic group is located at the end of pendant group X distant from B.

Preferably X is a group of formula

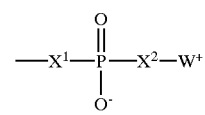

(VI)

in which the moieties $X^1$ and $X^2$, which are the same or different, are —O—, —S—, —NH— or a valence bond, preferably —O—, and $W^+$ is a group comprising an ammonium, phosphonium or sulphonium cationic group and a group linking the anionic and cationic moieties which is preferably a $C_{1-12}$-alkylene group.

Preferably W contains as cationic group an ammonium group, more preferably a quaternary ammonium group.

The group W⁺ may for example be a group of formula

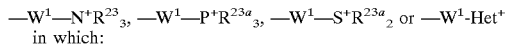

in which:

W¹ is alkylene of 1 or more, preferably 2–6 carbon atoms optionally containing one or more ethylenically unsaturated double or triple bonds, disubstituted-aryl, alkylene aryl, aryl alkylene, or alkylene aryl alkylene, disubstituted cycloalkyl, alkylene cycloalkyl, cycloalkyl alkylene or alkylene cycloalkyl alkylene, which group W¹ optionally contains one or more fluorine substituents and/or one or more functional groups; and either the groups $R^{23}$ are the same or different and each is hydrogen or alkyl of 1 to 4 carbon atoms, preferably methyl, or aryl, such as phenyl or two of the groups $R^{23}$ together with the nitrogen atom to which they are attached form a heterocyclic ring containing from 5 to 7 atoms or the three groups $R^{23}$ together with the nitrogen atom to which they are attached form a fused ring structure containing from 5 to 7 atoms in each ring, and optionally one or more of the groups $R^{23}$ is substituted by a hydrophilic functional group, and the groups $R^{23a}$ are the same or different and each is $R^{23}$ or a group $OR^{23}$, where $R^{23}$ is as defined above; or Het is an aromatic nitrogen-, phosphorus- or sulphur-, preferably nitrogen-, containing ring, for example pyridine.

Preferably W¹ is a straight-chain alkylene group, most preferably 1,2-ethylene.

Most preferred groups are the groups of formula (IVA), (IVB), (IVC), (IVD) and (IVE) as defined below: monomers containing such groups may be used alone or in combination with further zwitterionic monomers to provide a copolymer. Of these groups (IVB) are particularly preferred.

The groups of formula (IVA) are:

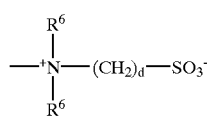

(IVA)

where the groups $R^6$ are the same or different and each is hydrogen or $C_{1-4}$ alkyl and d is from 2 to 4.

Preferably the groups $R^6$ are the same. It is also preferable that at least one of the groups $R^6$ is methyl, and more preferable that the groups $R^6$ are both methyl.

Preferably d is 2 or 3, more preferably 3.

When X is a group of formula (IVA) preferably B is a group of formula $-(CR^3{}_2)-$ or $-(CR^3{}_2)_2-$, eg. $-(CH_2)-$ or $-(CH_2CH_2)-$.

The groups of formula (IVB) are:

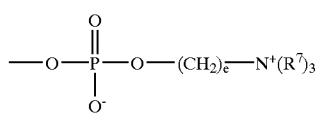

(IVB)

were the groups $R^7$ are the same or different and each is hydrogen or $C_{1-4}$ alkyl, and e is from 1 to 4.

Preferably the groups $R^7$ are the same. It is also preferable that at least one of the groups $R^7$ is methyl, and more preferable that the groups $R^7$ are all methyl.

Preferably e is 2 or 3, more preferably 2.

When X is a group of formula (IVB) preferably B is a group of formula $-(CR^3{}_2)-$ or $-(CR^3{}_2)_2-$, eg. $-(CH_2)-$ or $-(CH_2CH_2)-$.

The groups of formula (IVC) are:

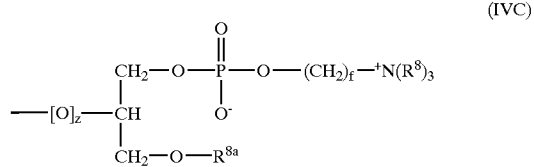

(IVC)

wherein the groups $R^8$ are the same or different and each is hydrogen or $C_{1-4}$ alkyl, $R^{8a}$ is hydrogen or, more preferably, a group $-C(O)B^1R^{8b}$ where $R^{8b}$ is hydrogen or methyl, preferably methyl, $B^1$ is a valence bond or straight or branched alkylene, oxaalkylene or oligo-oxaalkalyene group, and f is from 1 to 4; and if B is other than a valence bond Z is 1 and if B is a valence bond Z is O, if X is directly bonded to an oxygen or nitrogen atom and otherwise Z is 1.

Preferably the groups $R^8$ are the same. It is also preferable that at least one of the groups $R^8$ is methyl, and more preferable that the groups $R^8$ are all methyl.

Preferably f is 1 or 2, more preferably 2.

Preferably $B^1$ is:

a valence bond;

an alkylene group of formula $-(CR^{3a}{}_2)_{aa}-$, wherein the groups $-(CR^{3a}{}_2)-$ are the same or different, and in each group $-(CR^{3a}{}_2)-$ the groups $R^{3a}$ are the same or different and each group $R^{3a}$ is hydrogen or $C_{1-4}$ alkyl, preferably hydrogen, and is from 1 to 12, preferably 1 to 6;

an oxaalkylene group such as alkoxyalkyl having 1 to 6 carbon atoms in each alkyl moiety, more preferably $-CH_2O(CH_2)_4-$; or an oligo-oxaalkylene group of formula $-[(CR^{4a}{}_2)_{ba}O]_{ca}-$ where the groups $-(CR^{4a}{}_2)-$ are the same or different and in each group $-(CR^{4a}{}_2)-$ the groups $R^{4a}$ are the same or different and each group $R^{4a}$ is hydrogen or $C_{1-4}$ alkyl, preferably hydrogen, and ba is from 1 to 6, preferably 2 or 3, and ca is from 1 to 12, preferably 1 to 6.

Preferred groups $B^1$ include a valence bond and alkylene, oxaalkylene and oligo-oxaalkylene groups of up to 12 carbon atoms.

Preferably B and $B^1$ are the same.

When X is a group of formula (IVC) preferably B is a group of formula $-[(CR^4{}_2CR^4{}_2)_cO_b]CR^4{}_2CR^4{}_2-$, eg. $-(CH_2CH_2O)_c(CH_2CH_2)-$.

The groups of formula (IVD) are:

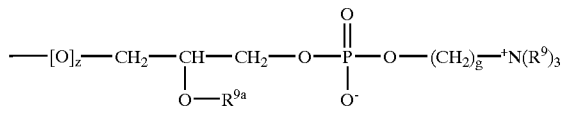

(IVD)

wherein the groups $R^9$ are the same or different and each is hydrogen or $C_1-C_4$ alkyl, $R^{9a}$ is a hydrogen or, more preferably, a group $-C(O)B^2R^{9b}$, $R^{9b}$ is hydrogen or methyl, preferably methyl, $B^2$ is a valence bond or a straight or branched alkylene, oxaalkylene or oligo—oxaalkylene group, and g is from 1 to 4; and if B is other than a valence bond Z is 1 and if B is a valence bond Z is 0 if X is directly bonded to an oxygen or nitrogen atom and otherwise Z is 1.

Preferably the groups $R^9$ are the same. It is also preferable that at least one of the groups $R^9$ is methyl, and more preferable that the groups $R^9$ are all methyl.

Preferably g is 1 or 2, more preferably 2.

Preferably $B^2$ is:

a valence bond;

an alkylene group of formula $—(CR^{3b}_2)_{ab}—$, wherein the groups $—(CR^{3b}_2)—$ are the same or different, and in each group $—(CR^{3b}_2)—$ the groups $R^{3b}$ are the same of different and each group $R^{3b}$ is hydrogen or $C_{1-4}$ alkyl, preferably hydrogen, and ab is from 1 to 12, preferably 1 to 6;

an oxaalkylene group such as alkoxyalkyl having 1 to 6, carbon atoms in each alkyl moiety, more preferably $—CH_2O(CH_2)_4—$; or an oligo-oxaalkylene group of formula $—[(CR^{4b}_2)_{bb}O]_{cb}—$ where the groups $—(CR^{4b}_2)—$ are the same or different and in each group $—(CR^{4b}_2)—$ the groups $R^{4b}$ are the same or different and each group $R^{4b}$ is hydrogen or $C_{1-4}$ alkyl, preferably hydrogen, and bb is from 1 to 6, preferably 2 or 3, and cb is from 1 to 12, preferably 1 to 6.

Preferred groups $B^2$ include a valence bond and alkylene, oxalkylene and oligo-oxalkylene groups of up to 12 carbon atoms.

Preferably B and $B^2$ are the same.

When X is a group of formula (IVD) preferably B is a group of formula $—[(CR^4_2CR^4_2)_bO]_cCR^4_2CR^4_2—$, eg. $—(CH_2CH_2O)_cCH_2CH_2—$.

The groups of formula (IVE) are:

$$\begin{array}{c} R^{10a}-O-CH_2 \quad\quad O \\ | \quad\quad\quad\quad || \\ CH-O-P-O-(CH_2)_hN^+(R^{10})_3 \\ | \quad\quad\quad\quad | \\ -[O]_z-CH_2 \quad\quad O^- \end{array} \quad (IVE)$$

wherein the groups $R^{10}$ are the same or different and each is hydrogen or $C_{1-4}$ alkyl, $R^{10a}$ is hydrogen or, more preferably, a group $—C(O)B^3R^{10b}$ where $R^{10b}$ is hydrogen or methyl, preferably methyl, $B^3$ is a valence bond or a straight or branched alkylene, oxaalkylene or oligo-oxaalkylene group, and h is from 1 to 4; and if B is other than a valence bond Z is 1 and if B is a valence bond Z is O if X is directly bonded to the oxygen or nitrogen and otherwise Z is 1.

Preferably the groups $R^{10}$ are the same. It is also preferable that at least one of the groups $R^{10}$ is methyl, and more preferable that the groups $R^{10}$ are all methyl.

Preferably h is 1 or 2, more preferably 2.

Preferably $B^3$ is:

a valence bond;

an alkylene group of formula $—(CR^{3c}_2)_{ac}—$, wherein the groups $—(CR^{3c}_2)—$ are the same or different, and in each group $—(CR^{3c}_2)—$ the groups $R^{3c}$ are the same or different and each group $R^{3c}$ is hydrogen or $C_{1-4}$ alkyl, preferably hydrogen, and ac is from 1 to 12, preferably 1 to 6;

an oxaalkylene group such as alkoxyalkyl having 1 to 6 carbon atoms in each alkyl moiety, more preferably $—CH_2O(CH_2)_4—$; or an oligo-oxaalkylene group of formula $—[(CR^{4c}_2)_{bc}O]_{cc}—$ where the groups $—(CR^{4c}_2)—$ are the same or different and in each group $—(CR^{4c}_2)—$ the groups $R^{4c}$ are the same or different and each group $R^{4c}$ is hydrogen or $C_{1-4}$ alkyl, preferably hydrogen, and bc is from 1 to 6, preferably 2 or 3, and cc is from 1 to 12, preferably 1 to 6.

Preferred groups $B^3$ include a valence bond and alkylene, oxaalkylene and oligo-oxaalkylene groups of up to 12 carbon atoms.

Preferably B and $B^3$ are the same.

When X is a group of formula (IVE) preferably B is a group of formula $—[(CR^4_2CR^4_2)_bO]_cCR^4_2CR^4_2—$, eg. $—(CH_2CH_2O)_cCH_2CH_2—$.

A polymer according to the invention is preferably formed from monomers including a comonomer of the formula $$\begin{array}{c} R^{14} \quad O \\ | \quad\quad || \\ CH_2=C-C-A^4-Q \end{array} \quad V$$

in which $R^{14}$ is hydrogen or a $C_{1-4}$-alkyl group $A^4$ is $—O—$ or $—NR^{15}—$ where $R^{15}$ is hydrogen, $C_{1-4}$-alkyl group or a group Q, and Q is selected from hydroxyl groups a straight or branched alkyl, alkoxyalkyl or (oligo-alkoxy) alkyl chain containing 1 to 24 carbon atoms unsubstituted or substituted by one or more fluorine atoms and optionally containing one or more carbon—carbon double or triple bonds;

a siloxane group $—(CR^{16a}_2)_{qq}(SiR^{16b}_2)(OSiR^{16b}_2)_{pp}R^{16b}$ in which each group $R^{16a}$ is the same or different and is hydrogen or alkyl of 1 to 4 carbon atoms or aralkyl, for example benzyl or phenethyl, each group $R^{16b}$ is alkyl of 1 to 4 carbon atoms, qq is from 1 to 6 and pp is from 0 to 49; and $C_{1-24}$-alkyl groups substituted with a group $Q^5$ selected from anionic groups selected from carboxylate, sulphonate, hydrogenphosphate and phosphate groups and cationic groups selected from $—N^+R^{31}_3$ in which each group $R^{31}_3$, in which each group $R^{31}$ is the same or different, and is hydrogen or alkyl of 1 to 6 carbon atoms two of which groups $R^{31}$ may together from a heterocyclic ring containing from 5 to 7 atoms, $^+$N Het where Het is an unsaturated heterocyclic group substituted or unsubstituted by one or more alkyl groups of 1 to 4 carbon atoms, and groups $P^+R^{32}_3$ in which each group $R^{32}$ is the same or different and is hydrogen or alkyl of 1 to 6 carbons atoms, two of which groups $R^{32}$ may together form a heterocyclic ring containing from 5 to 7 atoms.

In the formula V, group $R^{14}$ is preferably selected from hydrogen and methyl. $A^4$ is preferably $—O—$.

In the monomer of formula V, the group Q is most conveniently a hydrophobic group, preferably an alkyl, a fluoroalkyl or a siloxane group.

Preferred monomers V are comonomers in which Q is a) an alkyl group which group optionally contains one or more etheric oxygen atoms and optionally one or more carbon—carbon double or triple bonds for instance which has 6 or more carbon atoms, or b) a fluoroalkyl group, preferably of 6 or more carbon atoms, which group optionally contains one or more etheric oxygen atoms and optionally one or more carbon—carbon double or triple bonds, or c) a siloxane group, containing up to 50 silicon atoms, preferably in a linear chain.

Preferably the alkyl or fluoroalkyl groups Q contains up to 24 carbon atoms, for instance up to 18 carbon atoms. For instance in the compound of the formula V, Q is a straight or branched alkyl, alkoxyalkyl or oligoalkoxyalkyl chain containing 1–24 carbon atoms, unsubstituted or substituted by one or more fluorine atoms and optionally containing one or more carbon—carbon double or triple bonds or is a siloxane group as defined above.

Most preferably Q is:

an alkyl group of formula —$(CR^{17}_2)_m CR^{17}_3$, wherein the groups —$(CR^{17}_2)$— are the same or different, and in each group —$(CR^{17}_2)$— the groups $R^{17}$ are the same or different and each group $R^{17}$ is hydrogen, fluorine or $C_{1-4}$ alkyl or fluoroalkyl and m is from 5 to 23 if Q contains no fluorine atoms or from 1 to 23, preferably 5 to 23, if Q contains one or more fluorine atoms;

an alkoxyalkyl having 1 to 12 carbon atoms in each alkyl moiety; unsubstituted or substituted by one or more fluorine atoms; or an (oligo-alkoxyl)alkyl group of formula —$[(CR^{18}_2)_n O]_o (CR^{18}_2)_n R^{18}$ where the groups —$(CR^{18}_2)$— are the same or different and in each group —$(CR^{18}_2)$— the groups $R^{18}$ are the same or different and each group $R^{18}$ is hydrogen, fluorine or $C_{1-4}$ alkyl or fluoroalkyl and n is from 2 to 6, preferably 3 to 4, and o is from 1 to 12.

Particularly preferred groups Q are straight chain alkyl or fluoroalkyl groups optionally containing one or more carbon—carbon double or triple bonds.

Where Q is a siloxane group as defined above, each group —$(CR^{16a}_2)$— may be the same or different, preferably the same, and preferably each group $R^{16a}$ is hydrogen. Preferably qq is from 2 to 4, and is most preferably 3. Each group —$(SiR^{16b}_2)$— may be the same or different, preferably the same, and preferably each group $R^{16b}$ is methyl. Preferably pp is from 4 to 29.

In one specific embodiment the group Q does not contain any ethylenic unsaturation, i.e. any carbon—carbon double or triple bonds.

Particular examples of comonomers containing an alkyl, fluoroalkyl or siloxane group include: methylmethacrylate, butylmethacrylate, n-dodecyl methacrylate, octadecyl methacrylate, hexadecyl methacrylate, 1H,1H,2H,2H-heptadecafluorodecyl methacrylate, p-octyl styrene, p-dodecyl styrene and monomethacryloxypropyl terminated siloxanes especially poly(dimethyl siloxanes). n-Dodecyl methacrylate is particularly preferred.

In the novel polymers, it is preferred that all of the groups $R^{26}$, $R^{19}$, R and $R^{14}$ represent the same meaning, preferably methyl. Preferably also the groups $A^1$, $A^2$, A and $A^4$ represent the same group, and are preferably, —O—. Where such common features are present in the monomers, it is believed that copolymerisation proceeds in an optimum fashion, since the monomers are likely to have similar reactivity ratios.

The polymers are made from their constituent monomers by radical polymerisation, typically using thermal, redox or photochemical initiation. The polymerisation conditions could be such that reaction between the silyl group of monomer of the formula II with the hydroxyl group of the monomer of the formula I does not take place to any significant extent during polymerisation.

For thermal polymerisation a temperature from 40 to 100° C., typically 50 to 80° C. is used. For photochemical polymerisation actinic radiation such as gamma, U.V., visible, or microwave radiation may be used. Typically U.V. radiation of wavelength 200 to 400 nm is used.

The polymerisation is generally performed in a reaction medium, which is for instance a solution or dispersion of the monomers in a liquid phase using as a solvent for example acetonitrile, dimethyl formamide, chloroform, dichloromethane, ethyl acetate, dimethyl sulphoxide, dioxan, benzene, toluene, tetrahydrofuran, or where the polymer does not contain groups which react with protic solvents, water or an alkanol containing from 1 to 4 carbon atoms, e.g. methanol, ethanol or propan-2-ol. Alternatively, a mixture of any of the above solvents may be used.

The polymerisation may be carried out in the presence of one or more polymerisation initiators, usually free radical generators, usually peroxides or azo initiators, such as benzoyl peroxide, 2,2'-azo-bis(2-methylpropionitrile) or benzoin methyl ether. Other polymerisation initiators which may be used are disclosed in "Polymer Handbook", 3rd edition, Ed. J. Brandrup and E. H. Immergut, Pub. Wiley-Interscience, New York, 1989.

Generally the polymerisation is performed for 1 to 72 hours, preferably 8 to 48, for instance 16 to 24 hours, and under an inert atmosphere of for example nitrogen or argon.

The polymer is generally purified by dialysis, precipitation in a non—solvent (e.g. diethyl ether or acetone) or ultrafiltration. The resulting polymer is generally dried under vacuum, eg. for 5 to 72 hours and has a molecular weight from 10,000 to 10 million, preferably from 20,000 to 1 million.

It is preferable for the monomer of the formula I to be present in a molar excess to the monomer of the formula II. The two monomers are generally provided in the polymer in amounts so as to give the desired level of crosslinking when the polymer is used. Preferably the molar ratio of the monomer of the formula I to the monomer of the formula II is in the range 1:2 to 10:1, preferably 1:1 to 10:1, most preferably 2:1 to 6:1.

Where a zwitterionic monomer of the formula III is included, it is generally contained in a molar quantity in the range 0.01%, preferably at least 1%, most preferably at least 5%, for instance at least 10%. The total amount is preferably less than 50%, for instance in the range 15 to 33%.

Where comonomer of the formula V is included in the polymer, it may be present in an amount in the range 1 to 99% by mole, most preferably in an amount in the range 1 to 95%, most preferably in the range 10 to 90%, for instance in the range 25 to 80%.

The amount of monomer of the formula II is generally at least 1%, preferably at least 2%, for instance in the range 3 to 10%. The amount of monomer of the formula I is generally higher than the molar amount of monomer of the formula II, since this tends to encourage complete reaction of the trialkoxy silyl group of the monomer of the formula II. The residual, uncrosslinked hydroxyl group of the monomer of formula I is not very reactive, so that its presence in the crosslinked product does not cause problems with reactive interactions with fluids or solid substrates with which it is in contact.

The crosslinkable polymer is of particular utility for coating applications. The present invention provides further coating compositions containing the crosslinkable polymer. Such compositions generally comprise a liquid vehicle within which the polymer is dissolved or dispersed. Preferably the liquid vehicle includes a solvent for the polymer in which the polymer is dissolved. For instance the solvent may be an aqueous based solvent, but is more likely to be an organic solvent, for instance an alcohol or ether solvent. Coating compositions may comprise other components which assist wetting of an underlying surface and/or coating integrity.

The present invention provides also processes in which substrates are coated with a liquid coating composition according to the invention, followed by a step in which solvent is removed from the coating, for instance by evaporation, and in which the polymer is, after coating, subjected to a crosslinking step in which it is subjected to conditions in which crosslinking takes place between the hydroxyl groups of the monomer of the formula I and one of the said $OR^{16}$ groups of monomer of the formula II. Such reaction conditions generally involve subjecting the polymer to raise temperature, for instance under reduced pressure to remove alcohol $R^{16}OH$ by-product.

For some coating processes, it may be desirable to polymerise the starting monomers and crosslink in a single step. In this case, a coating composition comprises monomers and, if necessary, a solvent for the monomers, and is subjected to conditions whereby reaction between the trialkoxysilyl group of monomer II and the hydroxyl group of monomer I takes place simultaneously with radical initiated polymerisation.

The use of monomers of the formula I in combination with the formula II gives very good crosslinking levels, whilst producing a polymer product which has good integrity, that is cohesion, but adequate flexibility. It therefore provides a good coating for use on compliant substrates, especially substrates which are subjected to lengthening or other dimensional change in use. For instance the substrate which is coated may be the metal of a stent or other biomedical device which is expanded in use. The substrate may be an elastomer, or a plastically expandable plastics material.

The invention is illustrated further in the following examples:

EXAMPLE 1

The following outlines an experiment concerning membranes with and without hydroxypropyl methacrylate (Hpm). The figures show the relative molar amounts.

Membranes prepared were:
- /001 2-(methacryloyloxyethyl)-2'-(trimethylammonium ethyl)phosphate inner salt:lauryl methacrylate:3-trimethoxysilylpropyl methacrylate 30:60:10
- /002 2-(methacryloyloxyethyl)-2'-(trimethylammonium ethyl)phosphate inner salt:lauryl methacrylate:3-trimethoxysilylpropyl methacrylate 32:63:5
- /003 2-(methacryloyloxyethyl)-2'-(trimethylammonium ethyl)phosphate inner salt:lauryl methacrylate:3-trimethoxysilylpropyl methacrylate 33:65:2
- /004 2-(methacryloyloxyethyl)-2'-(trimethylammonium ethyl)phosphate inner salt:lauryl methacrylate:3-trimethoxysilylpropyl methacrylate:hydroxypropyl methacrylate 29:59:2:10
- /005 2-(methacryloyloxyethyl)-2'-(trimethylammonium ethyl)phosphate inner salt:lauryl methacrylate:3-trimethoxysilylpropyl methacrylate:hydroxypropyl methacrylate 23:47:5:25.

Method:
Moulds were prepared by laminating glass sheets with polyethylene terephthalate (PET) film using spray mount. The moulds were assembled using a PTFE spacer. The monomer solutions were injected into the moulds and allowed to polymerise at 50 C for 16 hours.

Observations:
Experiment /001 yielded polymer films on every occasion, however, the film obtained in each case was brittle and shattered on handling.

Experiment /002 on some occasions yielded a film that was isolable whilst on other occasions resulted in a tacky film which could not be removed from the PET even after swelling in water for 16 hours.

Experiment /003 consistently resulted in a tacky film which could not be removed from the PET.

Experiment /004 still continued to result in tacky films even with the inclusion of Hpm.

Experiment /005 gave clear films on every occasion which were elastic and exhibited some good wear and tear strength properties.

EXAMPLE 2

This example illustrates a process in which the polymers are preformed and then coated. The polymerisation uses free radical solution polymerisation techniques following the standard method outlined below.

A triple-necked round bottom flask (250 ml) was equipped with a Davis condenser, a nitrogen inlet, the, polymerization solvent which is ethanol and a thermometer. The condenser was topped with a calcium chloride guard tube, and a magnetic follower was added to the flask. The reaction system then purged using nitrogen gas.

The zwitterionic monomer was weighed and then stirred in the reaction solvent until dissolved. The comonomers were weighed and then stirred into the reaction solvent until dissolved. The initiator used throughout the polymer development was AIBN at a level of 2 w/w %, and this was dissolved into the reaction solvent.

The solutions were then filtered under vacuum using a buchner funnel, into the reaction vessel. The solution was degassed using a constant flow of nitrogen for a period of twenty minutes, after which time the nitrogen flow rate was reduced and the temperature increased to 62 C. The polymerisation was carried out under an atmosphere of nitrogen, and maintained at 62 C for When the polymerisation had finished the heat source was removed and the solution was allowed to cool to room temperature. The solvent was removed using rotary evaporation techniques until the point at which the polymer began to foam. This solution was then further diluted with dichloromethane and precipitated by dropwise addition into acetone with constant stirring. The precipitate was then collected using vacuum filtration under a blanket of nitrogen and dried at 25 C in vacuo for 16 hours.

The polymer was then cooled using liquid nitrogen and ground to a fine powder using an analytical mill. The polymer was then further dried in vacuo at 25 C for 16 hours. The yield of polymer obtained was recorded.

Ethanol was the reaction solvent.

The technique could be used to produce polymers having the molar ratios of example 1. When used to make a polymer having the monomer ratios of example 1/005, it produced a product having the following properties:

Elemental Analysis:

|  | C | H | N | P | Si |
|---|---|---|---|---|---|
| Theoretical | 62.59 | 9.91 | 1.37 | 3.02 | 0.60 |
| Actual | 60.65 | 9.88 | 1.43 | 3.06 | 0.59 |

|          | Dilute Viscosity Measurements: | | |
|----------|---------------------|-------------------|---------|
| Batch No. | Intrinsic Viscosity | Relative Viscosity | MV |
| 1 | 0.1455 | 1.145 | 172769 |
| 2 | 0.1404 | 1.140 | 1609190 |
| 3 | 0.1433 | 1.143 | 167718 |

Mv is Viscosity Average Molecular Weight and is expressed in Daltons.

The polymer was coated using dip coating from ethanol at 5 and 10 mg/ml. The coating speed was 3mm/min. The polymer was cross—linked by heating at 70 C for 4 hours or longer eg overnight.

The polymer was then used to coat a number of steel coronary devices crosslinked by heating and submitted to a number of tests which looked at the performance of the hydrogel coating during in vitro testing.

All of the SEM microscopy was carried out using a Hitachi S4000 field emission SEM. The samples were prepared by mounting on the stubs using conductive graphite pads. Sputter coating was not used.

Molecular weight, radius of gyration and second virial coefficients for the polymers were calculated from Zimm plots obtained through the use of static light scattering. The measurements were made using a PL-LSP light scattering photometer starting at 30° and increasing in 15° increments. The polymers were measured in ethanol with toluene used as the reference. A refractometer was used to establish the dn/dc value for the solutions.

Fibrinogen adsorption uses an assay similar to that used in our application WO93/01221.

RESULTS AND DISCUSSIONS

Molecular weights for the polymer was found to be in the region of 200,000 daltons, with a radius of gyration of 14 nm.

The biological performance (fibrinogen adsorption) of the novel polymers has been shown to be comparable to that of phosphorylcholine group containing copolymers currently used by Biocompatibles. The adsorption value was about 0.2 (comparative unit relating to absorbance in an ELISA test) for both PC polymers and about 1.8 for the uncoated steel.

An important property required of the final polymer coating is its mechanical stability. The angioplasty devices undergo several deformations and stresses when deployed, as such any coating must respond to these conditions. This is demonstrated in experiments, where coronary stents were coated with the hydroxyalkyl/reactive silyl copolymer and a more brittle coating not containing the hydroxypropyl methacrylate monomer. The more brittle polymer coating ruptures under the stresses associated with balloon expansion. This is not the case when stents coated with the new polymer are subjected to the procedure.

What is claimed is:

1. A cross-linkable polymer formed from monomers including
   a) a hydroxyl-group containing monomer of the formula I

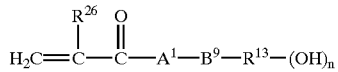

in which $R^{26}$ is hydrogen or a $C_{1-4}$-alkyl group;
$A^1$ is —O— or —$NR^{27}$— where $R^{27}$ is hydrogen or a $C_{1-4}$-alkyl group or a group $B^9R$—$(OH)_n$;
$B^9$ is a bond, a straight or branched alkylene, oxa alkylene or oligooxa alkylene group;
$R^{13}$ is a n+1 functional $C_{2-6}$ alkylene group, and n is an integer of one or more;

b) a reactive monomer of the formula (II)

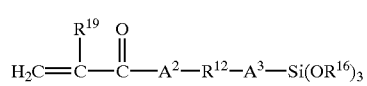

in which $R^{19}$ is hydrogen or a $C_{1-4}$-alkyl group;
$A^2$ is —O— or —$NR^{21}$— where $R^{21}$ is hydrogen, or a $C_{1-4}$-alkyl group
$R^{12}$ is a $C_{1-24}$ straight or branched alkylene, oxaalkylene or oligo oxaalkylene group in which each alkylene group has 1 to 6 carbon atoms;
$A^3$ is a bond or —O—; and
each $R^{16}$ is independently selected from $C_{1-6}$-alkyl groups; and c) a zwitterionic monomer of the formula (III)

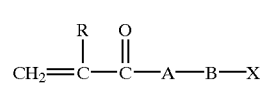

wherein B is a straight or branched alkylene, oxaalkylene or oligo-oxaalkylene chain optionally containing one or more fluorine atoms up to and including perfluorinated chains or, if X contains a carbon—carbon chain between B and the zwitterionic moiety, a valence bond;
X is a zwitterionic group
R is hydrogen or a $C_1$–$C_4$ alkyl group; and
A is —O— or —$NR^1$— where $R^1$ is hydrogen or a $C_1$–$C_4$ alkyl group or $R^1$ is —B—X where B and X are as defined above.

2. A polymer according to claim 1 in which the zwitterionic group X is a group in which the cationic moiety is based on a quaternary ammonium group and the anionic moiety is based on a phosphate group.

3. A polymer according to claim 1 in which the zwitterionic group is selected from group consisting of IVA, IVB, IVC, IVD and IVE in which
   i) the group of formula (IVA) are:

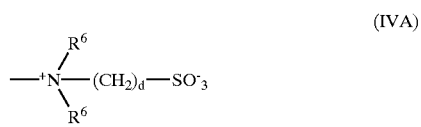

where the groups $R^6$ are the same or different and each is hydrogen or a $C_{1-4}$ alkyl group, and
d is from 2 to 4;

ii) the group of formula (IVB) are:

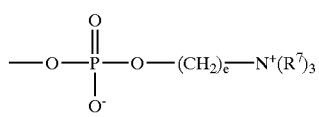
(IVB)

where the groups $R^7$ are the same or different and each is hydrogen or a $C_{1-4}$ alkyl group, and
e is from 1 to 4;

iii) the group of formula (IVC) are:

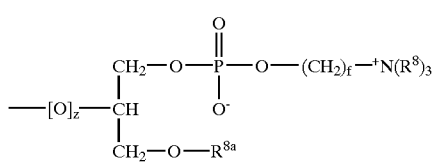
(IVC)

wherein the groups $R^8$ are the same or different and each is hydrogen or a $C_{1-4}$ alkyl group,
$R^{8a}$ is hydrogen or a group $—C(O)B^1R^{8b}$ where $R^{8b}$ is hydrogen or a methyl group,
$B^1$ is a valence bond or straight or branched alkylene, oxaalkylene or oligo-oxaalkalyene group,
f is from 1 to 4; and
if B is other than a valence bond, z is 1 and if B is a valence bond, z is 0, if X is directly bonded to an oxygen or nitrogen atom and otherwise z is 1;

iv) the group of formula (IVD) are:

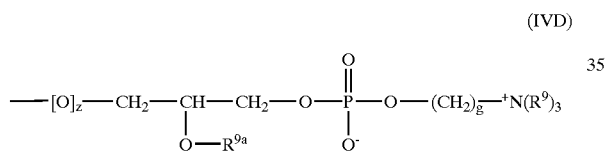
(IVD)

wherein the groups $R^9$ are the same or different and each is hydrogen or a $C_1$–$C_4$ alkyl group,
$R^{9a}$ is a hydrogen or a group $—C(O)B^2R^{9b}$, $R^{9b}$ is hydrogen or a methyl group,
$B^2$ is a valence bond or a straight or branched alkylene, oxaalkylene or oligo-oxaalkylene group;
g is from 1 to 4; and
if B is other than a valence bond, z is 1 and if B is a valence bond, z is 0 if X is directly bonded to an oxygen or nitrogen atom and otherwise z is 1;

v) the group of formula (I'VE) are:

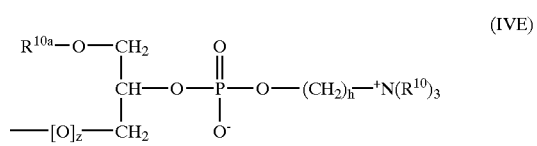
(IVE)

wherein the groups $R^{10}$ are the same or different and each is hydrogen or a group $—C(O)B^3R^{10b}$ where $R^{10b}$ is hydrogen or a $C_{1-4}$ alkyl group,
$R^{10a}$ is hydrogen or a methyl group,
$B^3$ is a valence bond or a straight or branched alkylene, oxaalkylene or oligo-oxaalkylene group;
h is from 1 to 4; and
if B is other than a valence bond, z is 1 and if B is a valence bond, z is 0 if X is directly bonded to the oxygen or nitrogen atom and otherwise z is 1.

4. A polymer according to claim 1 in which the monomers include a comonomer of the formula V

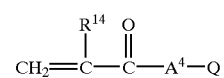
V in which $R^{14}$ is hydrogen or a $C_{1-4}$-alkyl group
$A^4$ is $—O—$ or $—NR^{15}—$ where $R^{15}$ is hydrogen, a $C_{1-4}$-alkyl group or a group Q, and Q is selected from hydroxyl groups;
a straight or branched alkyl, alkoxyalkyl or (oligo-alkoxy) alkyl chain containing 1 to 24 carbon atoms unsubstituted or substituted by one or more fluorine atoms and optionally containing one or more carbon—carbon double or triple bonds;
a siloxane group $—(CR^{16b}_2)_{qq}(SiR^{16b}_2)(OSiR^{16b}_2)_{pp}R^{16b}$ in which each group $R^{16a}$ is the same or different and is hydrogen or an alkyl group of 1 to 4 carbon atoms or an aralkyl group, each group $R^{16b}$ is an alkyl group of 1 to 4 carbon atoms, qq is from 1 to 6 and pp is from 0 to 49, and
$C_{1-24}$-alkyl groups substituted with a group $Q^5$ selected from anionic groups selected from carboxylate, sulphonate, hydrogenphosphate and phosphate groups and cationic groups $—^+NR^{31}_3$ in which each group $R^{31}$ is the same or different, and is hydrogen or an alkyl group of 1 to 6 carbon atoms two of which groups $R^{31}$ may together form a heterocyclic ring containing from 5 to 7 atoms, $—^+NHet$ where Het is an unsaturated heterocyclic group substituted or unsubstituted by one or more alkyl groups of 1 to 4 carbon atoms, and groups $—P^+R^{32}_3$ in which each group $R^{32}$ is the same or different and is hydrogen or an alkyl group of 1 to 6 carbons atoms, two of which groups $R^{32}$ may together form a heterocyclic ring containing from 5 to 7 atoms.

5. A coating composition comprising a liquid vehicle and a polymer according to claim 1 dissolved or dispersed in the vehicle.

6. A composition according to claim 5 in which the liquid vehicle includes a solvent for the polymer in which the polymer is dissolved.

7. A crosslinked polymer formed by subjecting a polymer according to claim 1 to condition such that cross-linking takes place between the OH group of monomer I and one of the said $OR^{16}$ groups of monomer II.

8. A process of polymerising monomers, comprising the step of radical polymerisation of:
a) a hydroxyl-group containing monomer of the formula I

in which $R^{26}$ is hydrogen or a $C_{1-4}$ alkyl group;
$A^1$ is $—O—$ or $—NR^{27}—$ where $R^{27}$ is hydrogen or a $C_{1-4}$-alkyl group or a group $B^9R—(OH)_n$;
$B^9$ is a bond, a straight or branched alkylene, oxa alkylene or oligooxa alkylene group;
$R^{13}$ is a n+1 functional $C_{2-6}$ alkylene group; and n is an integer of one or more; and b) a reactive monomer of the formula (II)

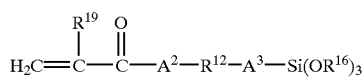

II in which $R^{19}$ is hydrogen or a $C_{1-4}$-alkyl group or;
$A^2$ is —O— or —NR$^{21}$— where $R^{21}$ is hydrogen or a $C_{1-4}$-alkyl group;
$R^{12}$ is $C_{1-24}$ straight or branched alkylene, oxaalkylene or oligo oxaalkylene group in which each alkylene group has 1 to 6 carbon atoms;
$A^3$ is a bond or —O—; and
each $R^{16}$ is independently selected from $C_{1-6}$-alkyl groups; and c) a zwitterionic monomer of the formula (III)

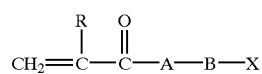

III wherein B is a straight or branched alkylene, oxaalkylene or oligo-oxaalkylene chain optionally containing one or more fluorine atoms up to and including perfluorinated chains or, if X contains a carbon—carbon chain between B and the zwitterionic moiety a valence bond;
X is a zwitterionic group
R is hydrogen or a $C_1$–$C_4$ alkyl group; and
A is —O— or —NR$^1$— where $R^1$ is hydrogen or a $C_1$–$C_4$ alkyl group or $R^1$ is —B—X where B and X are as defined above.

9. A process of cross-linking a polymer according to claim 1 in which the polymer is subjected to conditions such that cross-linking takes place between the OH group of monomer I and one of the said OR$^{16}$ groups of monomer II.

10. A process according to claim 9 further comprising the step of coating the polymer on a substrate prior to the cross-linking reaction.

11. A product comprising a substrate coated with a cross-linked polymer which is formed by crosslinking a polymer according to claim 1.

12. A polymer according to claim 2 in which the zwitterionic group is an ammonium phosphate ester group.

13. A polymer according to claim 3 in which the zwitterionic group X is of the formula IVB in which each of the groups $R^7$ is a $C_{1-4}$ alkyl group.

14. A polymer according to claim 13 in which each of the groups $R^7$ is a methyl group.

15. A polymer according to claim 14 in which e is 2 or 3.

16. A polymer according to claim 14 in which the monomers include 1 to 95% by mole of a comonomer of the formula V

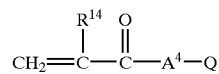

V in which $R^{14}$ is hydrogen or a $C_{1-4}$-alkyl group
$A^4$ is —O— or —NR$^{15}$— where $R^{15}$ is selected from the group consisting of hydrogen, a $C_{1-4}$-alkyl group and a group Q,
and Q is selected from the group consisting of
hydroxyl groups;

straight and branched alkyl, alkoxyalkyl and (oligoalkoxy)alkyl groups containing 1 to 24 carbon atoms unsubstituted or substituted by one or more fluorine atoms and optionally containing one or more carbon—carbon double or triple bonds;

siloxane groups —(CR$^{16a}_2$)$_{qq}$(SiR$^{16b}_2$)(OSiR$^{16b}_2$)$_{pp}$R$^{16b}$ in which each group $R^{16a}$ is the same or different and is selected from the group consisting of hydrogen, an alkyl group of 1 to 4 carbon atoms and an aralkyl group, each group $R^{16b}$ is an alkyl group of 1 to 4 carbon atoms, qq is from 1 to 6 and pp is from 0 to 49; and $C_{1-24}$-alkyl groups substituted with a group $Q^5$ selected from anionic groups selected from carboxylate, sulphonate, hydrogenphosphate and phosphate groups and cationic groups —$^+$NR$^{31}_3$ in which each group $R^{31}$ is the same or different, and is hydrogen or an alkyl group of 1 to 6 carbon atoms, two of which groups $R^{31}$ may together form a heterocyclic ring containing from 5 to 7 atoms, —$^+$NHet where Het is an unsaturated heterocyclic group substituted or unsubstituted by one or more alkyl groups of 1 to 4 carbon atoms, and groups —P$^+$R$^{32}_3$ in which each group $R^{32}$ is the same or different and is hydrogen or an alkyl group of 1 to 6 carbons atoms, two of which groups $R^{32}$ may together form a heterocyclic ring containing from 5 to 7 atoms.

17. A polymer according to claim 4 in which Q is an alkyl group (CR$^{17}_2$)$_m$CR$^{17}_3$ wherein the groups CR$^{17}_2$ are the same or different and in each group CR$^{17}_2$ the groups $R^{17}$ are the same or different, each group $R^{17}$ is selected from the group consisting of hydrogen, fluorine and a $C_{1-4}$-alkyl and -fluoroalkyl group and m is 5 to 23.

18. A polymer according to claim 17 in which each $R^{17}$ is hydrogen.

19. A cross-linkable polymer formed from monomers including
a) a hydroxyl-group containing monomer of the general formula I

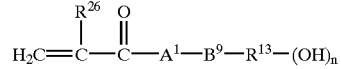

in which $R^{26}$ is hydrogen or a $C_{1-4}$-alkyl group;
$A^1$ is —O— or —NR$^{27}$— where $R^{27}$ is selected from the group consisting of hydrogen, a $C_{1-4}$-alkyl group and a group B$^9$R—(OH)$_n$;
B$^9$ is selected from the group consisting of a bond, and a straight and branched alkylene, oxa alkylene and oligooxa alkylene group;
$R^{13}$ is a n+1 functional $C_{1-24}$ alkylene group which may be substituted, and
n is an integer of 1 or more;

b) 2 to 10% by mole of a reactive monomer of the general formula (II)

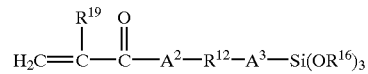

II in which $R^{19}$ is hydrogen or a $C_{1-4}$-alkyl group;
$A^2$ is —O— or —NR$^{21}$— where $R^{21}$ is selected from the group consisting of hydrogen, and a $C_{1-4}$-alkyl group;
$R^{12}$ is selected from the group consisting of a $C_{1-24}$ straight and branched alkylene, oxaalkylene and oligo oxaalkylene group in which each alkylene group or moiety has 1 to 6 carbon atoms;

$A^3$ is a bond or —O—; and
each $R^{16}$ is independently an $C_{1-6}$-alkyl group;

c) a zwitterionic monomer of the general formula (III)

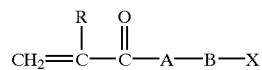
III wherein B is selected from the group consisting of a straight and branched alkylene, oxaalkylene and oligo-oxaalkylene group optionally containing one or more fluorine atoms up to and including perfluorinated chains and, if X contains a carbon—carbon chain between B and the zwitterionic moiety, a valence bond;
X is a zwitterionic group
R is hydrogen or a $C_1$–$C_4$ alkyl group; and
A is —O— or —$NR^1$— where $R^1$ is selected from the group consisting of hydrogen and a $C_1$–$C_4$ alkyl group and —B—X where B and X are as defined above; and d) a comonomer of the formula V

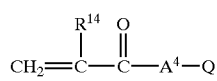
V in which $R^{14}$ is hydrogen or a $C_{1-4}$-alkyl group
$A^4$ is —O— or —$NR^{15}$— where $R^{15}$ is selected from the group consisting of hydrogen, a $C_{1-4}$-alkyl group and a group Q, and
Q is an alkyl group $(CR^{17}_2)_m CR^{17}_3$ wherein the groups $CR^{17}_2$ are the same or different and in each group $CR^{17}_2$ the groups $R^{17}$ are the same or different, each group $R^{17}$ is selected from the group consisting of hydrogen, fluorine and a $C_{1-4}$-alkyl and -fluoroalkyl group and m is 5 to 23.

20. A polymer according to claim 19 in which each $R^{17}$ is hydrogen.

21. A polymer according to claim 20 in which the zwitterionic group is selected from groups IVA, IVB, IVC, IVD and IVE in which i) the groups of formula (IVA) are:

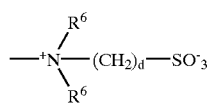
(IVA)

where the groups $R^6$ are the same or different and each is hydrogen or a $C_{1-4}$ alkyl group and
d is from 2 to 4;

ii) the groups of formula (IVB) are:

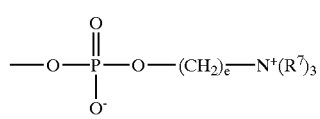
(IVB)

where the groups $R^7$ are the same or different and each is hydrogen or a $C_{1-4}$ alkyl group, and
e is from 1 to 4;

iii) the groups of formula (IVC) are:

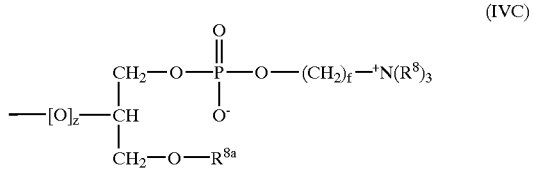
(IVC)

wherein the groups $R^8$ are the same or different and each is hydrogen or a $C_{1-4}$ alkyl group,
$R^{8a}$ is hydrogen or a group —$C(O)B^1R^{8b}$ where $R^{8b}$ is hydrogen or a methyl group,
$B^1$ is selected from the group consisting of a valence bond, and a straight and branched alkylene, oxaalkylene and oligo-oxaalkylene group,
f is from 1 to 4; and
if B is other than a valence bond, z is 1 and if B is a valence bond, z is 0;

iv) the groups of formula (IVD) are:

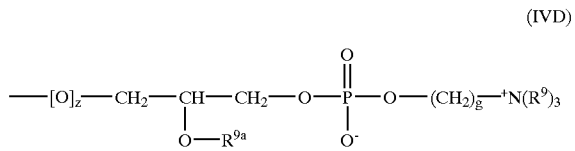
(IVD)

wherein the groups $R^9$ are the same or different and each is hydrogen or a $C_1$–$C_4$ alkyl group,
$R^9$ is a hydrogen or a group —$C(O)B^2R^{9b}$, $R^{9b}$ is hydrogen or a methyl group,
$B^2$ is selected from the group consisting of a valence bond and a straight and branched alkylene, oxaalkylene and oligo-oxaalkylene group;
g is from 1 to 4; and
if B is other than a valence bond, z is 1 and if B is a valence bond, z is 0;

v) the groups of formula (IVE) are:

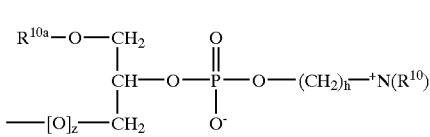
(IVE)

wherein the groups $R^{10}$ are the same or different and each is hydrogen or a group —$C(O)B^3R^{10b}$ where $R^{10b}$ is hydrogen or a $C_{1-4}$ alkyl group,
$R^{10a}$ is hydrogen or a methyl group,
$B^3$ is selected from a valence bond and straight and a branched alkylene, oxaalkylene and oligo-oxaalkylene group;
h is from 1 to 4; and
if B is other than a valence bond, z is 1 and if B is a valence bond, z is 0.

22. A polymer according to claim 21 in which the zwitterionic group X is of the formula IVB in which each of the groups $R^7$ is a $C_{1-4}$ alkyl group.

23. A coating composition comprising a liquid vehicle and a polymer according to claim 16.

24. A cross-linked polymer formed by subjecting a polymer according to claim 16 to conditions such that cross-linking takes place between the OH group of monomer I and one of the said $OR^{16}$ groups of monomer II.

25. A process of crosslinking a polymer according to claim 16 in which the polymer is subjected to conditions such that crosslinking takes place between the OH group derived from the monomer of the formula I and one of the said $OR^{16}$ groups.

26. A process of crosslinking a polymer according to claim 19 in which the polymer is subjected to conditions such that crosslinking takes place between the OH group derived from the monomer of the formula I and one of the $OR^{16}$ groups.

27. A process according to claim 25 in which the conditions include heating the polymer to a temperature of about 70° C.

28. A product comprising a substrate coated with crosslinked polymer formed by crosslinking a polymer according to claim 16.

29. A process according to claim 26 in which conditions include heating the polymer to a temperature of about 70° C.

* * * * *

UNITED STATES PATENT AND TRADEMARK OFFICE
CERTIFICATE OF CORRECTION

| | |
|---|---|
| PATENT NO. | : 6,673,883 B1 |
| DATED | : January 6, 2004 |
| INVENTOR(S) | : Lee Rowan |

Page 1 of 1

It is certified that error appears in the above-identified patent and that said Letters Patent is hereby corrected as shown below:

Title page,
Item [63], Related U.S. Application Data, should read
-- Continuation-in-part of application No. 09/011,523, filed April 28, 2998, now U.S. Patent No. 6,083,257 --

Column 1,
Before line 1, should read
   -- This is a continuation-in-part of U.S. Application No. 09/011,523, filed April 28, 1998, which was the National Stage Entry under §371 of International Application No. PCT/GB/96/0289, filed November 1, 1996, and which is now U.S. Patent No. 6,083,257; for which reissue Application No. 10/180,060 was filed on June 27, 2002. --

Signed and Sealed this

Twelfth Day of April, 2005

JON W. DUDAS
*Director of the United States Patent and Trademark Office*